United States Patent
Lee et al.

(10) Patent No.: US 10,335,087 B2
(45) Date of Patent: Jul. 2, 2019

(54) BIOSIGNAL PROCESSING APPARATUS AND BIOSIGNAL PROCESSING METHOD

(71) Applicant: SAMSUNG ELECTRONICS CO., LTD., Suwon-si (KR)

(72) Inventors: Joonhyung Lee, Yongin-si (KR); Sangkyu Kim, Yongin-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 151 days.

(21) Appl. No.: 14/669,200

(22) Filed: Mar. 26, 2015

(65) Prior Publication Data

US 2016/0058381 A1 Mar. 3, 2016

(30) Foreign Application Priority Data

Aug. 27, 2014 (KR) .......................... 10-2014-0112333

(51) Int. Cl.
  *A61B 5/00* (2006.01)
  *A61B 5/053* (2006.01)

(52) U.S. Cl.
  CPC ............ *A61B 5/6843* (2013.01); *A61B 5/681* (2013.01); *A61B 5/7221* (2013.01); *A61B 5/742* (2013.01); *A61B 5/053* (2013.01); *A61B 5/7405* (2013.01)

(58) Field of Classification Search
  CPC ....... A61B 5/6843; A61B 5/681; A61B 5/742; A61B 5/7221; A61B 5/053; A61B 5/1455; A61B 5/14532; A61B 5/14546; A61B 5/0059; A61B 2562/0247; A61B 5/6844; A61B 2562/0233; A61B 2562/146; A61B 5/6824; A61B 5/6886; A61B 5/7405
  See application file for complete search history.

(56) References Cited

U.S. PATENT DOCUMENTS

| | | | |
|---|---|---|---|
| 6,424,851 B1 | 7/2002 | Berman et al. | |
| 8,352,004 B2* | 1/2013 | Mannheimer | A61B 5/6831 600/310 |
| 8,546,761 B2 | 10/2013 | Aeschbach | |
| 9,558,336 B2* | 1/2017 | Lee | A61B 5/681 |
| 2009/0312615 A1* | 12/2009 | Caduff | A61B 5/6843 600/316 |
| 2013/0037719 A1 | 2/2013 | Melling et al. | |
| 2015/0265190 A1* | 9/2015 | Ikebe | A61B 5/6843 600/316 |

FOREIGN PATENT DOCUMENTS

| | | | |
|---|---|---|---|
| JP | 2001-91452 A | * | 4/2001 |
| JP | 2004298408 A | * | 10/2004 |
| JP | 2008-134132 A | | 6/2008 |

OTHER PUBLICATIONS

Machine translation of JP 2004298408 A.*

* cited by examiner

*Primary Examiner* — David J. McCrosky
(74) *Attorney, Agent, or Firm* — Sughrue Mion, PLLC

(57) ABSTRACT

Provided are a biosignal processing apparatus and a biosignal processing method. The biosignal processing apparatus includes: a first measurement module configured to detect a biosignal of a subject in a non-invasive manner in response to the biosignal processing apparatus being in contact with the subject; a second measurement module configured to measure a contact state with respect to the subject; and a controller configured to determine whether the contact state is equal to or greater than a reference value.

13 Claims, 6 Drawing Sheets

BIOSIGNAL PROCESSING APPARATUS AND BIOSIGNAL PROCESSING METHOD

CROSS-REFERENCE TO RELATED APPLICATION

This application claims priority from Korean Patent Application No. 10-2014-0112333, filed on Aug. 27, 2014 in the Korean Intellectual Property Office, the disclosure of which is incorporated herein in its entirety by reference.

BACKGROUND

1. Field

The present disclosure relates to biosignal processing apparatuses and biosignal processing methods for measuring a contact state with respect to a subject when measuring a biosignal.

2. Description of the Related Art

With advances in medicine and increased life spans, interest in health care is increasing. In this regard, interest in medical appliances is also increasing. Examples of such medical appliances include various medical appliances used in hospitals or clinics, small and medium sized medical appliances installed in public institutions or the like, small sized medical appliances and health care devices that may be possessed or carried by individuals.

In medical appliances or medical examinations, various invasive measurement methods are widely used. For example, a blood sample is collected from a subject and measurement and analysis are performed on the collected blood sample. By measuring a concentration of a specific material within the blood sample, it is possible to determine a health condition related thereto. However, such an invasive measurement method may cause pain during blood collection and require to run a colorimetric assay to determine the concentration of a specific material in the blood sample.

As a non-invasive method, biosignal detection methods are being studied. However, a non-invasive method has a higher error occurrence probability than an invasive method. For example, a measurement apparatus may be incorrectly positioned while being used.

SUMMARY

Provided are biosignal processing apparatuses and biosignal processing methods for measuring a contact state with respect to a subject.

Additional aspects will be set forth in part in the description which follows and, in part, will be apparent from the description, or may be learned by practice of the presented exemplary embodiments.

According to an aspect of an exemplary embodiment, a biosignal processing apparatus includes: a first measurement module configured to detect a biosignal of a subject in a non-invasive manner in response to the biosignal processing apparatus being in contact with the subject; a second measurement module configured to measure a contact state of the biosignal processing apparatus with respect to the subject; and a controller configured to determine whether the contact state is equal to or greater than a reference value.

When the contact state is less than the reference value, the controller may generate an indicator indicating information about the contact state.

The biosignal processing apparatus may further include an output module that outputs the indicator.

The output module may include at least one selected from a display module that displays the indicator and a sound output unit that outputs the indicator as an audible sound.

When the contact state is equal to or greater than the reference value, the controller may control the first measurement module to detect the biosignal of the subject.

The second measurement module may include at least one selected from the group consisting of an optical sensor, a touch sensor, and a pressure sensor.

The first measurement module may include an attenuated total reflection (ATR) prism that is contactable with the subject and attenuates a light beam incident thereon.

A contact surface of the second measurement module with respect to the subject may be disposed on a same plane as a contact surface of the ATR prism with respect to the subject.

The second measurement module may be disposed at an edge of the ATR prism.

The first measurement module may include: a light source that radiates a light beam to the subject through the ATR prism; and a detector that detects a light beam reflected or scattered from the subject through the ATR prism.

The first measurement module may include one or more electrode pairs that are contactable with the subject.

A contact surface of the second measurement module with respect to the subject may be disposed on a same plane as a contact surface of the electrode pairs with respect to the subject.

The first measurement module may include: one or more electrode pairs; a current supplier that supplies a current to the one or more electrode pairs; and a detector that detects a change in the current, which is caused by the subject, from the electrode pairs.

According to an aspect of another exemplary embodiment, a biosignal processing method of a biosignal processing apparatus may include: measuring a contact state of the biosignal processing apparatus with respect to a subject; and measuring a biosignal of the subject in a non-invasive manner when the contact state is equal to or greater than a reference value.

The biosignal processing method may further include: outputting an indicator indicating information about the contact state when the contact state is less than the reference value.

The outputting of the indicator may include at least one selected from displaying the indicator in a form of a text or an image, and outputting the indicating as an audible sound.

The contact state may be a contact state of an ATR prism that attenuates a light beam incident thereon.

The measuring of the contact state may include measuring a contact state of a sensor with respect to the substrate, which is disposed on a same plane as a contact surface of the ATR prism with respect to the subject.

The sensor may include at least one selected from the group consisting of an optical sensor, a touch sensor, and a pressure sensor.

The sensor may be disposed at an edge of the ATR prism.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
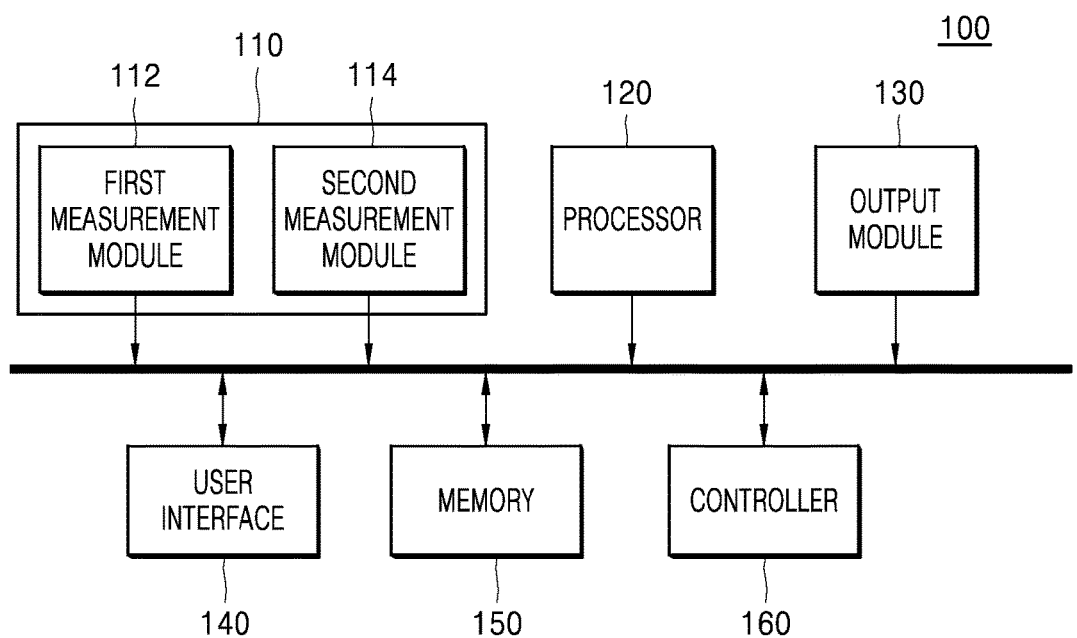
FIG. 1 is a block diagram of a biosignal processing apparatus.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects.

FIG. 1 is a block diagram of a biosignal processing apparatus 100. As shown in FIG. 1, the biosignal processing apparatus 100 may include a measurement module 110 that measures a biosignal of a subject and a contact state with respect to the subject, a processor 120 that processes the biosignal received from the measurement module 110, an output module 130 that outputs information about the processed biosignal and the contact state, a user interface 140 that receives a user input or the like, a memory 150 that stores a program to be used in the biosignal processing apparatus 100, and a controller 160 that controls internal components of the biosignal processing apparatus 100.

The biosignal processing apparatus 100 may be implemented using a single housing. The biosignal processing apparatus 100 may be a device capable of being carried by a subject, that is, a user. For example, the biosignal processing apparatus 100 may be a wearable device. In addition, the biosignal processing apparatus 100 may be implemented using a plurality of housings. In a case where the biosignal processing apparatus 100 is implemented using a plurality of housings, components may be connected to one another by wire or wireless. The biosignal processing apparatus 100 may be implemented using a partial configuration of a device that performs a different function, for example, a mobile terminal.

The measurement module 110 may include a first measurement module 112 that measures the biosignal of the subject, and a second measurement module 114 that measures the contact state with respect to the subject. The measurement module 110 is detachable from the subject. For example, the measurement module 110 may be worn on a user's wrist, chest, or ankle.

A biosignal is a signal in a subject such as, for example, a human, an animal, or a body part of the human or the animal, which can be continually measured and monitored. The biosignal is a unique signal generated from the subject. For example, the biosignal may be a signal based on a movement of a specific part (for example, a heart or a muscle) of the subject, such as an electrocardiogram (ECG), a ballistocardiogram (BCG), a photoplethysmograph (PPG), or an electromyogram (EMG), a blood pressure, and the biosignal may be information about an amount of materials included in the subject, for example, a blood sugar, a cholesterol, and a body fat. The user may be the subject from which a biosignal is to be measured, but the user is a medical expert having an ability to use the biosignal processing apparatus 100. That is, the user may be a broader concept than the subject.

The first measurement module 112 may measure the biosignal in a non-invasive manner. The first measurement module 112 may include a plurality of electrodes 400. The plurality of electrodes 400 may contact the subject when the subject wears the first measurement module 112. The first measurement module 112 may detect the biosignal by measuring an electrical property from a change in the biosignal. For example, the first measurement module 112 may detect the biosignal by measuring a change in a resistance. Besides the electrodes 400, the first measurement module 112 may measure the biosignal by using a light beam, such as an infrared ray. The first measurement module 112 may measure a single biosignal (for example, a blood sugar), but embodiments are not limited thereto. The first measurement module 112 may measure a plurality of biosignals (for example, a blood sugar level, a blood pressure, and the like), and separate modules may be provided for each biosignal.

The second measurement module 114 may measure a contact state with respect to the subject. In a case where the user loosely wears the measurement module 100, the contact state may be indicated as poor because a source signal (e.g., a light beam or an electromagnetic signal) of the first measurement module 112 may be scatted through a gap between the measurement module 110 and the skin of the user. In that case, noise or an error may occur. On the other hand, if the user tightly wears the measurement module 110, the contact state may be indicated as good because the source signal of the first measurement module 112 is directly applied to the subject. The second measurement module 114 may be disposed adjacent to the first measurement module 112 to measure the contact state with respect to the subject. The contact state of the second measurement module 114 may mean a contact state between the first measurement module 112 and the subject. The second measurement module 114 may be an optical sensor (for example, an illumination sensor), a touch sensor, and a pressure sensor.

The processor 120 may process the detected biosignal. For example, in a case where the biosignal indicates a blood sugar level, the processor 120 may calculate a blood sugar pattern over time by using the detected biosignal and determine whether the blood sugar pattern of the subject is normal. In addition, in a case where the biosignal is an ECG signal, the processor 120 may amplify the ECG signal after receiving it from the first measurement module 112 and filter the amplified ECG signal by using a finite-impulse response (FIR) bandpass filter. Then, the processor 120 may generate an ECG signal pattern by detecting peaks from the filtered ECG signal and adaptively filtering the detected peaks.

The output module 130 may output information about the biosignal or the contact state. The output module 130 may include at least one selected from a display module that displays the above-described information in a form of an image or a text, and a sound output unit that outputs the above-described information as an audible sound.

The display module may display a user interface (UI) or a graphical user interface (GUI) so as to display the information about the biosignal or the contact state. The display module may include at least one selected from the group consisting of a liquid crystal display (LCD), a thin film transistor-liquid crystal display (TFT-LCD), an organic light-emitting diode (OLED), a flexible display, and a three-dimensional (3D) display. Two or more display modules may be provided, depending on an implementation mode of the biosignal processing apparatus 100.

The display module may constitute a touch screen by forming a mutual layer structure together with a touch pad that receives a user input. In a case where the display module and the touch pad form the mutual layer structure to thereby constitute the touch screen, the display module may also be used as an input device as well as an output unit. In an exemplary embodiment, the display module constituted as the touch screen may automatically start to measure the biosignal when a user touch input is detected in a certain region.

The sound output unit may output the information about the biosignal or the contact state as an audible sound. The sound output unit may include a speaker, a buzzer, or the like.

The memory 150 may store data generated during operations of the biosignal processing apparatus 100. According to an exemplary embodiment, the memory 150 is a general storage medium and may include a hard disk drive (HDD), a read only memory (ROM), a random access memory (RAM), a flash memory, and a memory card.

The user interface 140 may receive an input for operating the biosignal processing apparatus 100 from the user, and may output at least one selected from the information about the biosignal processed by the biosignal processing apparatus 100 and the information about the contact state. The user interface 140 may include a button, a keypad, a switch, a dial, or a touch interface, which allows the user to directly operate the biosignal processing apparatus 100. The user interface 140 may include a display that displays an image and may be implemented using a touch screen. According to another exemplary embodiment, the user interface 140 may include an I/O port that connects human interface devices (HIDs). The user interface 140 may include an I/O port that inputs or outputs an image.

The controller 160 may control an overall operation of the biosignal processing apparatus 100. For example, the controller 160 may perform control such that the first measurement module 112 measures the biosignal. However, before controlling the first measurement module 112, the controller 160 may determine whether the contact state with respect to the subject is equal to or greater than a reference value, based on the measurement result of the second measurement module 114. When the contact state with respect to the subject is less than the reference value, the controller 160 may provide the result to the user through the output module 130. When the contact state with respect to the subject is equal to or greater than the reference value, the first measurement module 112 may measure the biosignal. The reference value may be preset and stored as a touch intensity, a pressure intensity, or an illumination intensity when the source of the first measurement module 112 is blocked from the outside.

Figure 2:
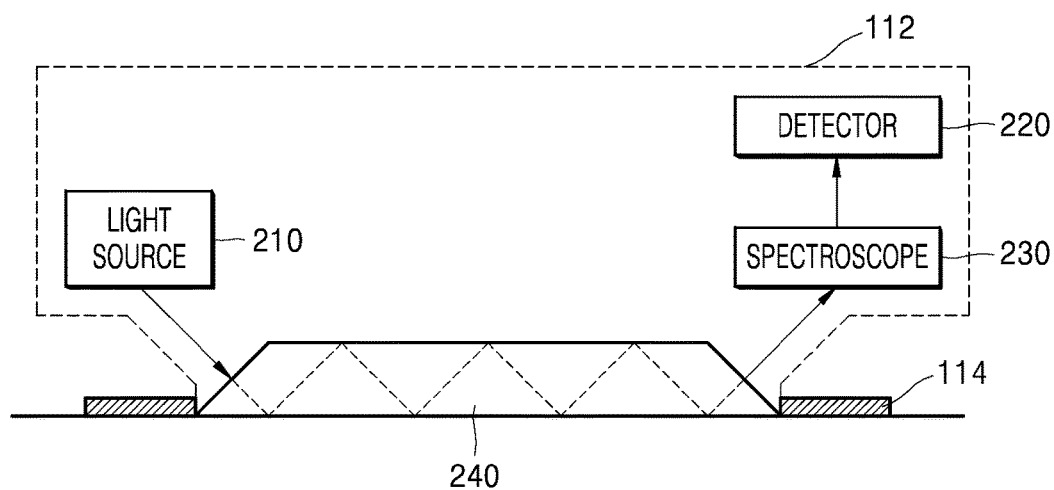
FIG. 2 is a diagram illustrating a relationship between a first measurement module and a second measurement module applicable to the biosignal processing apparatus of FIG. 1.

As described above, the biosignal processing apparatus 100 may tightly contact the subject so as to prevent outside air from being introduced between the biosignal processing apparatus 100 and the subject. FIG. 2 is a diagram illustrating a relationship between the first measurement module 112 and the second measurement module 114 that are applied to the biosignal processing apparatus of FIG. 1. As illustrated in FIG. 2, the first measurement module 112 may include a light source 210 that generates a light beam, and a detector 220 that detects a light beam that is radiated from the light source 210 and is reflected or scattered from a subject 10. The first measurement module 112 may further include a spectroscope 230 that splits a light beam reflected or scattered from the subject 10. The light beam split by the spectroscope 230 may be detected by the detector 220.

The light beam generated by the light source 210 may be an infrared ray. A depth or range of a measurement region of the subject 10 may be changed according to a wavelength of the infrared ray. For example, a mid-infrared ray may be used to measure a biosignal with respect to an epidermal region of the subject 10 or a biosignal with respect to a part of an epidermal region and a dermal region of the subject 10. The mid-infrared ray may have a wavelength of about 2.5 μm to about 20 μm and have a penetration depth of about 50 μm to about 100 μm with respect to a skin. The mid-infrared ray may be used to analyze molecular structures of solid, liquid, and gas. Since the mid-infrared ray forms a narrow and sharp peak in spectrum data, the mid-infrared ray may be advantageous to component determination and quantification of a material containing complicated components. The light beam is not limited to the mid-infrared ray. As the light beam, a near-infrared ray may be used.

The first measurement module 112 may include an attenuated total reflection (ATR) prism 240. The ATR prism 240 may contact the surface of the subject 10 (surface on which the detection is performed). The light beam generated by the light source 210 may be emitted to the outside of the ATR prism 240 through the ATR prism 240, and the emitted light beam may be split by the spectroscope 230 and be detected by the detector 220. While the light beam is reflected within the ATR prism 240, an evanescent wave W may be generated toward the subject 10. Due to the evanescent wave W, the measurement and detection of the subject 10 adjacent thereto may be more effectively performed.

Figure 3:
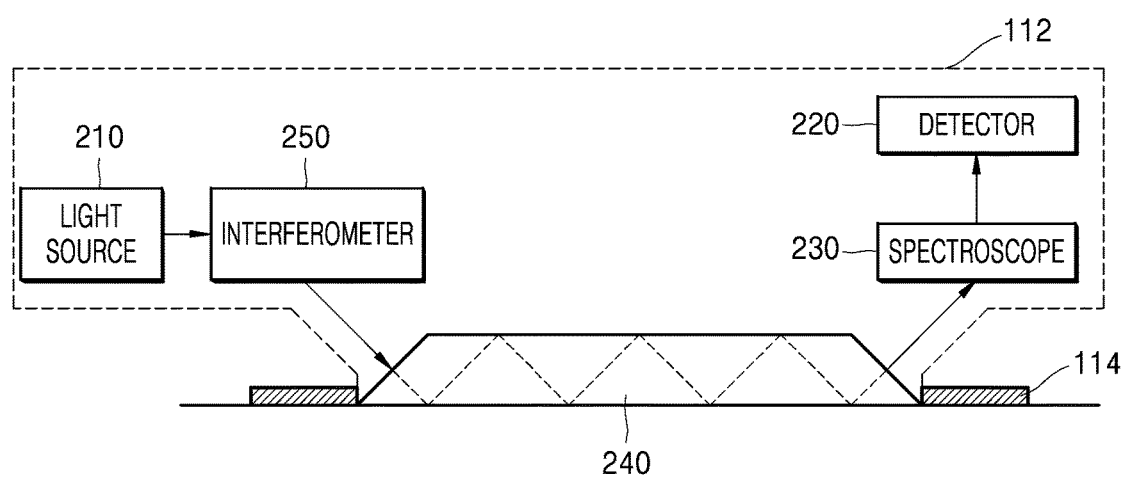
FIG. 3 is a diagram illustrating a relationship between a first measurement module and a second measurement module applicable to the biosignal processing apparatus of FIG. 1.

FIG. 3 is a diagram illustrating a relationship between a first measurement module 112 and a second measurement module 114 in another example applied to the biosignal processing apparatus of FIG. 1. As compared with the first measurement module 112 illustrated in FIG. 2, the first measurement module 112 illustrated in FIG. 3 may further include an interferometer 250. The light beam generated by the light source 210 may be radiated to the subject 10 through the interferometer 250. Since the interferometer 250 is included in the first measurement module 112, the first measurement module 112 may have a high signal-to-noise ratio (SNR) and a high resolution characteristic.

In FIGS. 2 and 3, the ATR prism 240 functions to transfer the light beam to the subject 10. If external materials are not introduced between the ATR prism 240 and the subject 10, the biosignal of the subject 10 may be more effectively measured. Thus, the ATR prism 240 may tightly contact the subject 10. Also, the ATR prism 240 may bend, curve, or stretch to cover any three-dimensional shape.

According to an exemplary embodiment, in order to determine whether the ATR prism 240 tightly contacts the subject 10, the biosignal processing apparatus 100 may further include the second measurement module 114. A contact surface of the second measurement module 114 with respect to the subject 10 may be disposed on the same plane as a contact surface of the ATR prism 240 with respect to the subject 10. The second measurement module 114 may include at least one selected from the group consisting of an optical sensor, a touch sensor, and a pressure sensor. When the ATR prism 240 tightly contacts the subject 10, the second measurement module 114 also may tightly contact the subject 10. Like the ATR prism 240, the second measurement module 114 may bend, curve, or stretch to cover any three-dimensional shape. When the ATR prism 240 is separated from the subject 10, the second measurement module 114 also may be separated from the subject 10.

Figure 4:
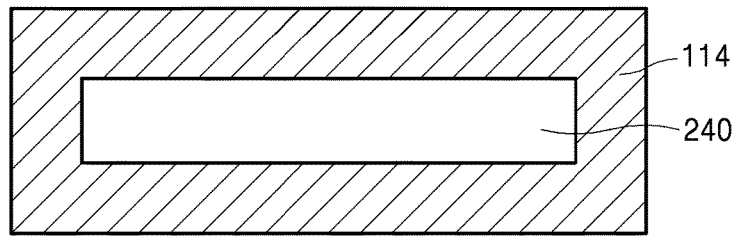
FIG. 4 is a plan view illustrating a relationship between an attenuated total reflection (ATR) prism and a second measurement module, according to an exemplary embodiment.

The second measurement module 114 may be disposed not to overlap the ATR prism 240 at the edge of the ATR prism 240. FIG. 4 is a plan view illustrating a relationship between the ATR prism 240 and the second measurement module 114, according to an exemplary embodiment. As illustrated in FIG. 4, the second measurement module 114 may be disposed to surround the ATR prism 240. The second measurement module 114 may include a plurality of sensors that are arranged at regular intervals to detect the contact state of the ATR prism 240. The second measurement module 114 may include a plurality of pressure sensors that are arranged at the outer periphery of the ATR prism 240 at regular intervals.

Figure 5:
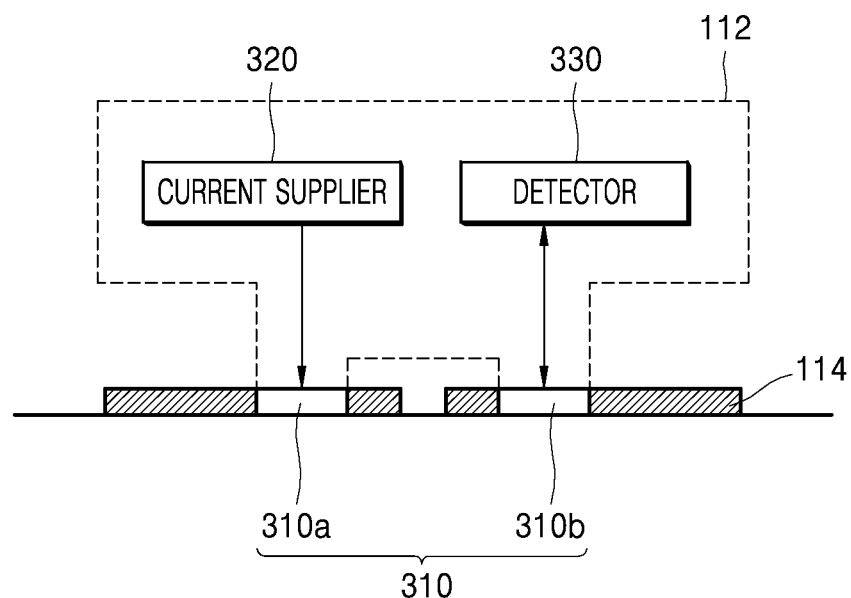
FIG. 5 is a diagram illustrating a relationship between a first measurement module and a second measurement module applicable to the biosignal processing apparatus of FIG. 1.

FIG. 5 is a diagram illustrating a relationship between the first measurement module 112 and the second measurement module 114 in another example that is applicable to the biosignal processing apparatus of FIG. 1. As illustrated in FIG. 5, the first measurement module 112 may include one or more electrode pairs 310 that are contactable with the subject 10, a current supplier 320 that supplies a current to the electrode pairs 310, and a detector 330 that detects a change in the current, which is caused by the subject 10, from the electrode pairs 310.

Figure 6:
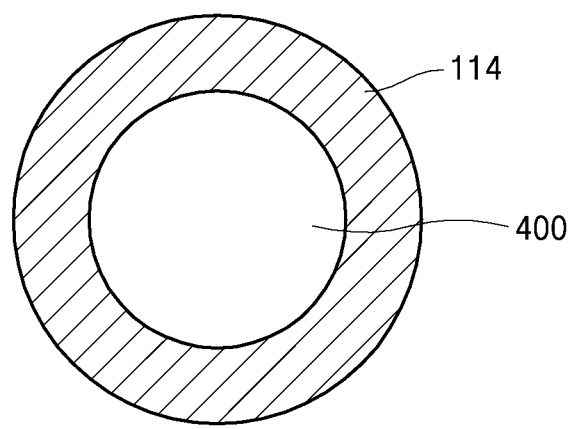
FIG. 6 is a plan view illustrating a relationship between an electrode and a second measurement module, according to an exemplary embodiment.

The one or more electrode pairs 310 may contact the subject 10. The change in the current applied to at least a part of the electrode pairs 310 may generate a change in electromagnetic energy in the subject 10, and the detector 330 may measure a biosignal by detecting the change in the electromagnetic energy. The second measurement module 114 may be disposed not to overlap the electrode 400 at the edge of the electrode 400. FIG. 6 is a plan view illustrating a relationship between the electrode 400 and the second measurement module 114, according to an exemplary embodiment. As illustrated in FIG. 6, the second measurement module 114 may be disposed to surround the electrode 400. The second measurement module 114 may include a plurality of sensors that are arranged at regular intervals to detect the contact state of the electrode 400. The electrode 400 may be the electrodes of the electrode pairs 310 illustrated in FIG. 5. On the other hand, since the electrode 400 is small in size, the second measurement module 114 may not surround the electrode 400. The second measurement module 114, for example, a touch sensor, an optical sensor, or a pressure sensor, may be arranged in parallel to the electrode 400.

Figure 7:
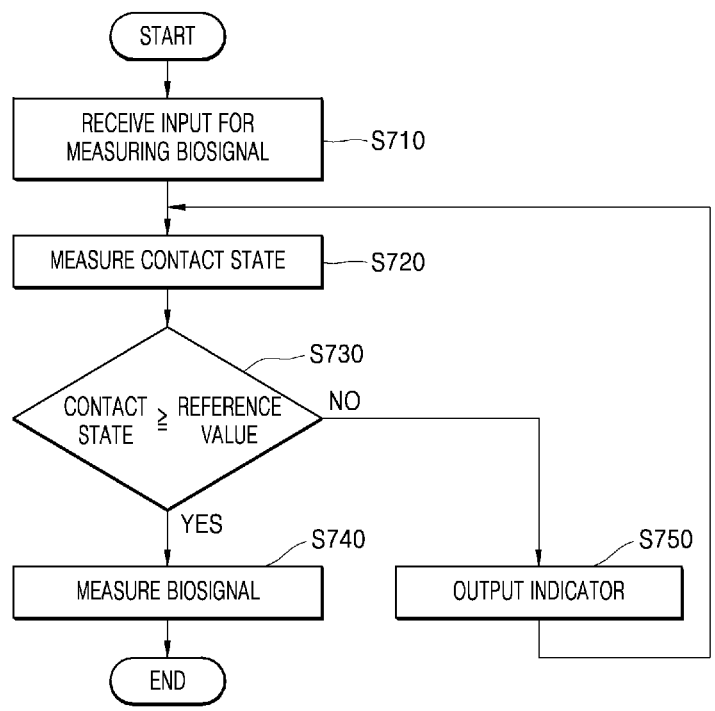
FIG. 7 is a flowchart of a biosignal processing method, according to an exemplary embodiment.

FIG. 7 is a flowchart of a biosignal processing method, according to an exemplary embodiment. First, an input for measuring a biosignal may be received (S710). A user may input a user command for measuring the biosignal through the user interface 140 of the biosignal processing apparatus 100. In addition, when the user wears the biosignal processing apparatus 100, the biosignal processing apparatus 100 may determine that the input for measuring the biosignal has been received.

The second measurement module 114 may measure the contact state with respect to the subject (S720). The second measurement module 114 may be an optical sensor, a touch sensor, or a pressure sensor. A contact surface of the second measurement module 114 with respect to the subject may be disposed on the same plane as a contact surface of the first measurement module 112 with respect to the subject. Therefore, the contact state of the second measurement module 114 with respect to the subject may be the contact state of the first measurement module 112 with respect to the subject.

The controller 160 may determine whether the contact state is equal to or greater than a reference value (S730). The term "contact state" used herein refers to a contact area of the ATR prism 240 that contacts the skin of the subject. For example, in a case where the second measurement module 114 is the touch sensor, the touch sensor may detect a change in an amount of charges, which is caused by the contact or non-contact with the subject, in a form of a voltage level. In a case where the second measurement module 114 includes a plurality of sensors, the controller 160 may compare detection results of the plurality of sensors with the reference value. The reference value is a threshold value when the sensor contacts the subject, and may be registered in advance.

When the contact state is equal to or greater than the reference value, the first measurement module 112 may measure the biosignal (S740). When the contact state is equal to or greater than the reference value, it may be determined that the first measurement module 112 correctly contacts the subject. Therefore, the first measurement module 112 may measure the biosignal, and the biosignal processing apparatus 100 may perform signal processing on the measured signal and output a signal processing result.

On the other hand, when the contact state is less than the reference value, the controller 160 may generate an indicator indicating that the contact state is bad (S750). The generated indicator may be output through the output unit.

Figure 8:
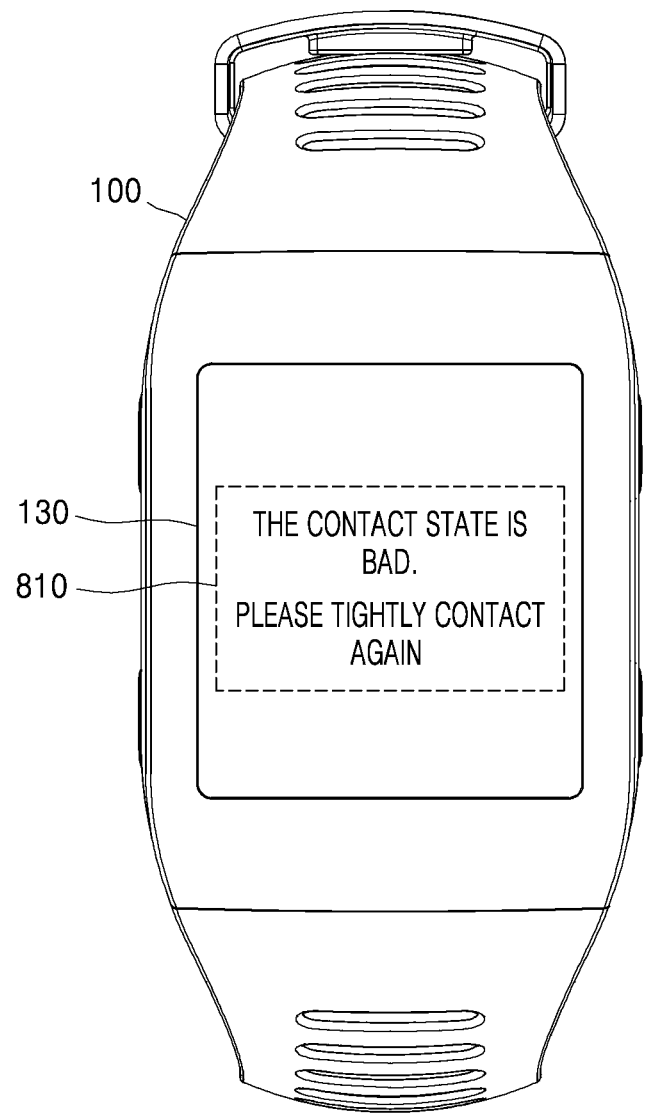
FIGS. 8 and 9 are reference diagrams describing a method of displaying an indicator, according to an exemplary embodiment.
Figure 9:
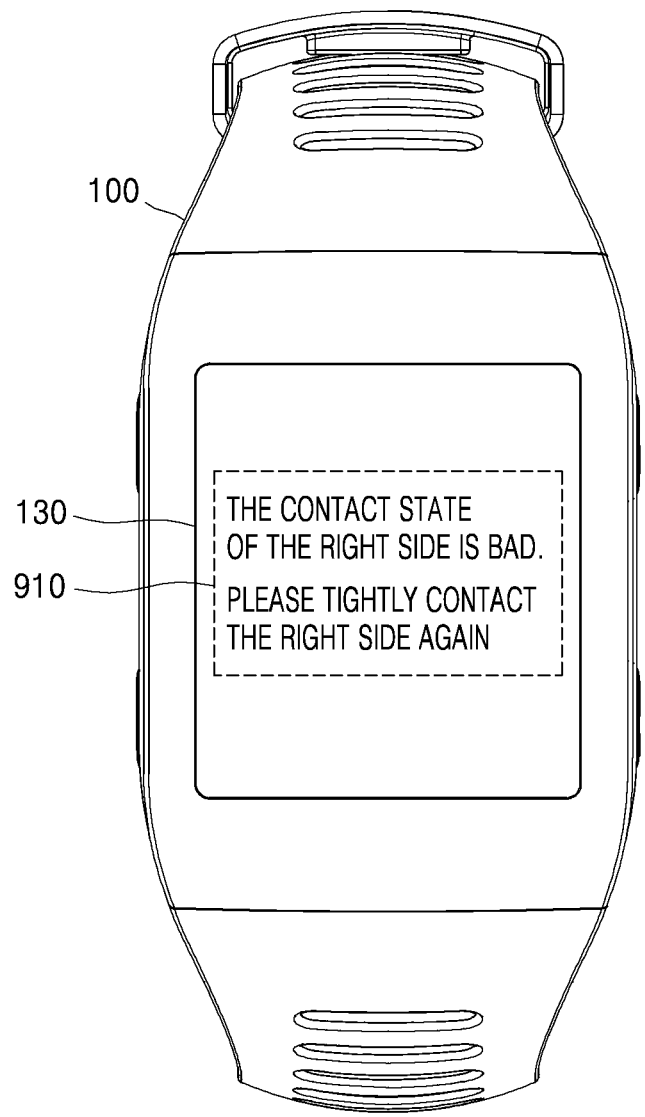

FIGS. 8 and 9 are reference diagrams of a method of displaying an indicator, according to an exemplary embodiment. As illustrated in FIG. 8, when the contact state is less than the reference value, the output unit of the biosignal processing apparatus 100 may display an indicator 810 that indicates information about the contact state to a user. The indicator may allow the user to check the contact state between the biosignal processing apparatus 100 and the subject. Alternatively, in a case where the second measurement module 114 includes a plurality of sensors, the controller 160 may monitor the contact state of each of the plurality of sensors and provide an indicator 910 that indicates information about a position at which the contact state is bad and guides a user's action as illustrated in FIG. 9.

As described above, according to the one or more of the above exemplary embodiment, it is possible to induce the user to correctly use the biosignal processing apparatus 100 by detecting the contact state between the measurement module and the subject and informing the detected contact state. In addition, it is possible to induce the user to correctly use the biosignal processing apparatus 100 by providing information about whether the measurement module contacts the subject.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A biosignal processing apparatus comprising:
   a biosignal measurement module that comprises a prism and a spectroscope and is configured to detect a biosignal of a subject in a non-invasive manner while the prism is in contact with the subject;
   a touch sensor configured to bend to cover a three-dimensional shape of the subject, measure a change in an amount of charges carried in the touch sensor, and determine a contact area between the prism and the subject based on the change in the amount of the charges carried in the touch sensor, a contact surface of the touch sensor and a contact surface of the prism being disposed on a same plane with respect to the subject while the contact areas of the touch sensor is being measured; and
   a controller configured to control the biosignal measurement module to start measuring the biosignal in response to determining that the contact area between the prism and the subject being equal to or greater than a reference value,
   wherein the touch sensor is disposed to surround the prism, and boundaries of the contact surface of the prism are entirely in contact with boundaries of the contact surface of the touch sensor.

2. The biosignal processing apparatus of claim 1, the controller is further configured to generate an indicator indicating information about a contact state of the biosignal measurement module in response to determining that the contact area being less than the reference value.

3. The biosignal processing apparatus of claim 2, further comprising a display configured to display the indicator.

4. The biosignal processing apparatus of claim 2, further comprising a speaker that outputs the indicator as an audible sound.

5. The biosignal processing apparatus of claim 1, wherein the prism is an attenuated total reflection (ATR) prism that is contactable with the subject and attenuates a light beam incident thereon.

6. The biosignal processing apparatus of claim 5, wherein the biosignal measurement module comprises:
   a light source that radiates a light beam to the subject through the ATR prism; and
   a detector that detects a light beam reflected or scattered from the subject through the ATR prism.

7. The biosignal processing apparatus of claim 1, wherein the biosignal measurement module comprises one or more electrode pairs that are contactable with the subject.

8. The biosignal processing apparatus of claim 7, wherein the contact surface of the touch sensor with respect to the subject is disposed on a same plane as a contact surface of the electrode pairs with respect to the subject.

9. The biosignal processing apparatus of claim 1, wherein the biosignal measurement module comprises:
   one or more electrode pairs;
   a current supplier that supplies a current to the one or more electrode pairs; and
   a detector that detects a change in the current, which is caused by the subject, from the electrode pairs.

10. A biosignal processing method of a biosignal processing apparatus including a prism and an touch sensor, the method comprising:
    measuring a change in an amount of charges carried in the touch sensor while a contact surface of the touch sensor and a contact surface of the prism are disposed on a same plane with respect to a subject;
    determining a contact area between the prism and the subject based on the change in the amount of the charges; and
    measuring a biosignal of the subject in a non-invasive manner in response to the determined contact area between the prism and the subject being equal to or greater than a reference value,
    wherein the measuring the change in the amount of the charges comprises measuring the change in the amount of the charges while the touch sensor is bend to cover a three-dimensional shape of the subject, and boundaries of the contact surface of the prism are entirely in contact with boundaries of the contact surface of the touch sensor.

11. The biosignal processing method of claim 10, further comprising:
    outputting an indicator indicating information about a contact state of the biosignal processing apparatus in response to determining that the contact area being less than the reference value.

12. The biosignal processing method of claim 11, wherein the outputting the indicator comprises at least one selected from:
    displaying the indicator in a form of a text or an image; and
    outputting the indicator as an audible sound.

13. The biosignal processing method of claim 10, wherein the contact area of the prism is a contact area of an attenuated total reflection (ATR) prism that attenuates a light beam incident thereon.

* * * * *